(12) United States Patent
Kusibojoska et al.

(10) Patent No.: US 6,981,968 B2
(45) Date of Patent: Jan. 3, 2006

(54) ABSORBENT ARTICLE WITH WAIST BELT

(75) Inventors: Liljana Kusibojoska, Hisings Kärra (SE); Peter Rönnberg, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 689 days.

(21) Appl. No.: 09/955,018

(22) Filed: Sep. 19, 2001

(65) Prior Publication Data

US 2002/0038110 A1 Mar. 28, 2002

Related U.S. Application Data

(60) Provisional application No. 60/234,970, filed on Sep. 25, 2000.

(51) Int. Cl.
A61F 13/15 (2006.01)

(52) U.S. Cl. ........................................ 604/392; 604/394
(58) Field of Classification Search ............ 604/385.24, 604/385.3, 386, 387, 391–394; 428/100
See application file for complete search history.

(56) References Cited

U.S. PATENT DOCUMENTS

| | | | |
|---|---|---|---|
| 1,388,529 A | | 8/1921 | Smith |
| 5,009,653 A | | 4/1991 | Osborn, III |
| 5,374,262 A | * | 12/1994 | Keuhn, Jr. et al. .......... 604/391 |
| 5,549,593 A | * | 8/1996 | Ygge et al. ................. 604/391 |
| 5,707,707 A | * | 1/1998 | Burnes et al. ................ 428/95 |
| 5,870,778 A | * | 2/1999 | Tharpe .......................... 2/400 |

FOREIGN PATENT DOCUMENTS

| | | |
|---|---|---|
| EP | 409307 | 1/1991 |
| EP | 589395 | 3/1994 |
| FR | 2794348 | 12/2000 |
| WO | 9817140 | 4/1998 |

OTHER PUBLICATIONS

U.S. Appl. No. 09/955,019, Liljana Kusibojoska and Peter Rönnberg, "Briefs for Supporting an Absorbent Article", filed Sep. 19, 2001.

* cited by examiner

*Primary Examiner*—Weilun Lo
*Assistant Examiner*—Catharine L Anderson
(74) *Attorney, Agent, or Firm*—Burns, Doane, Swecker & Mathis, L.L.P.

(57) ABSTRACT

An absorbent article with a longitudinal direction and a transverse direction includes a liquid-permeable cover sheet, a liquid-tight cover sheet, and an absorption body enclosed between the cover sheets, and has two side edges extending in the longitudinal direction and two end edges extending in the transverse direction. The article includes a waist belt having a first fastening member having a surface provided with fastening loops to cooperate with a fastening member having hook members and are arranged in a number of chain-like rows of loops. The chain-like rows of loops are arranged principally in the longitudinal direction of the article, and, in addition, a second fastening member arranged to cooperate with the first fastening member in order to fasten the article into a shape similar to underpants.

12 Claims, 3 Drawing Sheets

ABSORBENT ARTICLE WITH WAIST BELT

CROSS-REFERENCE TO RELATED APPLICATIONS

The present application claims the benefit of U.S. Provisional Application No. 60/234,970, filed in the United States on Sep. 25, 2000. The contents of U.S. Provisional Application No. 60/234,970 are hereby incorporated herein by reference.

BACKGROUND OF THE INVENTION

1. Technical Field

The invention relates to an absorbent article with a longitudinal direction and a transverse direction, comprising a liquid-permeable cover sheet, a liquid-tight cover sheet, and an absorption body enclosed between the cover sheets, and having two side edges extending in the longitudinal direction and two end edges extending in the transverse direction, which article comprises a waist belt formed by at least one material layer and arranged substantially parallel to an end edge of the article, and having members for fastening the waist belt around a user's waist, and the article comprises members for fastening the article into a shape similar to underpants.

2. Description of Related Art

It has become increasingly common for diapers and incontinence pads, for example, of the type which are fastened together during use so that the diaper or incontinence pad encloses the user's pelvic area in the manner of absorbent underpants, to be provided with fastening arrangements of the hook-and-loop type. Such a fastening arrangement comprises a fastening member having a surface provided with loop-elements and designed to cooperate with a fastening member having a surface provided with hooks or hook-like projections, which can hook securely on the surface provided with loop-elements.

The fastening members of the loop type that have been available to date generally consist of a laminate of a carrier material, such as a plastic film or a nonwoven material, and a loop material, such as a loosely knitted or woven textile material or a loosely bonded nonwoven material. However, a disadvantage of fastening members comprising a plastic layer is that they are not permeable to air and vapor, which means that an absorbent article provided with such a fastening member can be unnecessarily airtight and uncomfortable to wear. This is particularly so in absorbent articles of the belt type, i.e., articles which are held by a belt which is secured around the user's waist. Such an article is advantageously provided with a belt of loop material, which makes it possible to adjust its size. It is desirable, in this case, that the belt material is smooth, soft and comfortable against the user's skin, that it does not have sharp or hard edges that can chafe the skin, and also that the belt material has a certain breathability and is able to let body moisture and air pass through. It is also desirable for the loop material to be inexpensive so that it can be used for disposable absorbent articles, i.e., those articles that are discarded after a single use and are not washed or reused.

OBJECTS AND SUMMARY

An object of the invention is, therefore, to make available an absorbent article with a waist belt comprising a fastening member provided with loops, which fastening member is soft and comfortable, air-permeable and vapor-permeable, has high tensile strength and sufficient stiffness to avoid deformation during use, and can be produced in a cost-effective manner.

An article designed according to the invention, and of the type discussed in the introduction, is principally distinguished by the fact that the waist belt comprises a first fastening member having a surface provided with fastening loops that are designed to cooperate with a fastening member comprising hook members and are arranged in a number of chain-like rows of loops, each formed by a continuous thread that penetrates through at least a material layer included in the waist belt. The chain-like rows of loops are arranged principally in the longitudinal direction of the article, at right angles to the direction of extent of the waist belt, and, in addition, a second fastening member is arranged on the end edge of the article opposite the waist belt, and has hook members that are arranged to cooperate with the first fastening member in order to fasten the article into a shape similar to underpants.

According to one embodiment of the invention, the waist belt comprises a fastening member provided with hook members that are arranged in the form of a fastening surface or a fastening flap at one end of the waist belt, which cooperate with the fastening member provided with loops on the waist belt in order to fasten the waist belt around a user's waist.

A suitable fastening member provided with loops for an article provided with a belt according to the invention is advantageously produced by means of one or more rows of loops being sewn securely into a layered carrier material. This affords several advantages. One advantage is that the fastening loops are anchored in a mechanical manner in the carrier material, which means that it is not necessary to use thermoplastic materials, adhesive or the like to secure the threads in the carrier material. However, it can be expedient for some components in either the thread and/or the carrier material to be thermoplastic, since it is then possible to secure cut-off or clipped-off thread ends by melting the thread end to the carrier material. Such melting can be carried out while the fastening member is cut to the right shape and size. Alternatively, it is possible to secure the cut-off thread ends with adhesive.

A further advantage of the fastening member described above is that it has a high degree of breathability because the carrier material is penetrated by the thread that forms the fastening loops. This makes the fastening member especially suitable for use in combination with absorbent articles in which the fastening member is arranged over a large area of skin, such as diapers and incontinence pads, which, by means of a waist belt, are secured in a shape similar to underpants. It has thus been found to be particularly expedient for the waist belt on such an article to be made up completely, or to a large extent, of a breathable fastening member provided with loops.

Since the fastening member is produced by sewing rows of loops into a carrier material, it is also possible to increase the bendability of a stiff material so that the material in the waist belt thereby bends more easily along bend lines which run parallel with the rows of loops. Correspondingly, the stiffness of the material increases transverse to the rows of loops. This feature can also be favorable when the fastening member is arranged in the form of a belt along the waist edge of a diaper. If the rows of loops are arranged principally at right angles to the waist edge, then the fastening member can follow the body and curves around the waist, while the material nearest to the waist edge does not bend, roll-up or crease. These phenomena often occur when the person using the absorbent article is overweight, and they cause a number of problems. For example, it becomes difficult to fasten the absorbent article. It is also uncomfortable to wear, and the risk of body fluid leaking out of the article increases considerably if the waist edge is folded out onto the outside of the diaper.

Suitable materials for use as a carrier material for a fastening member provided with loops are layered materials such as plastic film, nonwoven, or a laminate of two or more layers of plastic film, nonwoven, tissue or the like. The carrier material preferably consists of a single layer of nonwoven with a stiffness of 0.10–0.70 N and preferably with a stiffness of 0.35 N, measured according to the CIRCULAR BEND PROCEDURE which is described in U.S. Pat. No. 5,009,653. This method is a modification of ASTM D 4032-82 and involves simultaneous deformation of a material in several directions, one of the surfaces of the specimen becoming concave and the opposite surface becoming convex. The method thus gives a force value which is a measure of the flexural resistance, or the average stiffness in all directions.

Particularly suitable carrier materials are nonwoven materials with a basis weight of from 40 g/m$^2$ to 80 g/m$^2$. Particularly suitable nonwoven materials are spunbond materials. In an absorbent article according to the invention, the carrier material constitutes all, or part, of the waist belt. This means that the thread, which is sewn through the carrier material and forms the fastening loops, can come to lie against the user's skin during use. For the thread to be comfortable against the user's skin, it must therefore be smooth and not too coarse. It is also preferable that the thread is not absorbent, so that liquid cannot be transported in the thread. However, it is possible to use absorbent thread material such as viscose and cotton. The absorption properties of the thread are of less importance in some designs, for example when the waist belt consists of two halves projecting from the side edges of the article. In such an embodiment, it is unlikely that the belt will come into contact with body fluid delivered to the article. Alternatively, the thread can be made of nylon, polyester, polyethylene, polypropylene, or the like. Voluminous threads comprising many substantially parallel fibers are preferred, and the thread's combined preferable coarseness is approximately 20–90 deniers.

The fastening loops expediently have a length of 2–10 millimeters. The length of a fastening loop refers to the distance between two points of penetration in a row of loops.

The loops of the fastening member are preferably arranged in substantially parallel rows with a spacing of 1–10 mm between the rows. It can also be advantageous to arrange rows of loops in groups of two or more rows with a greater spacing between the groups than between the rows included in the groups. By grouping the rows of loops, it is possible to obtain a waist belt having zones with different properties, for example different fastening capacity, different breathability, and different stiffness. The rows of loops can thus be distributed uniformly across the entire surface of the waist belt or, alternatively, only be provided on those parts of the waist belt which are expected to be used for fastening the article. In a second embodiment, the rows of loops are located at the free end portions of the waist belt and form at least one group of at least two rows of loops at each end portion.

According to a further embodiment, the fastening member comprises at least two groups of rows of loops, the rows of loops within the groups being located at a mutual spacing of 1–10 mm, and the spacing between the groups being greater than the spacing between the rows of loops in the groups, namely 5–100 mm.

The waist belt can either comprise a continuous and contiguous band of material or of two belt halves that project principally at right angles from each side edge at one end edge of the article. A contiguous waist belt is intended to signify a belt that extends along the whole waist edge of the article and thus comes to extend the whole way round the user's waist when the article is in use. Such a waist belt can, however, consist of several parts that are joined together and have different properties.

As is evident from the above, the waist belt can be made of different types of material in different parts of the belt. Thus, the end portions of the belt can consist of a perforated material which is provided with loops and which permits fastening and stiffening, while a portion of the belt situated centrally between the end portions can differ in terms of properties such as elasticity, compressibility, breathability, stiffness, or the like. The belt can have different properties in different areas depending on the closeness between the rows of loops, the size of the loops, etc. Alternatively, the belt can consist of parts that have different properties from each other and have been joined together to form a contiguous waist belt, or belt halves.

To make it easier to anchor cut-off thread ends and to prevent the rows of fastening loops from being unraveled, it is advantageous if the thread and/or the carrier material comprises a thermoplastic component that can be used for thermally bonding the thread ends in the carrier material.

BRIEF DESCRIPTION OF THE FIGURES

The invention will now be described in greater detail with reference to the illustrative embodiments shown in the attached drawings, in which.

DETAILED DESCRIPTION OF THE PREFERRED EMBODIMENTS

Figure 1:
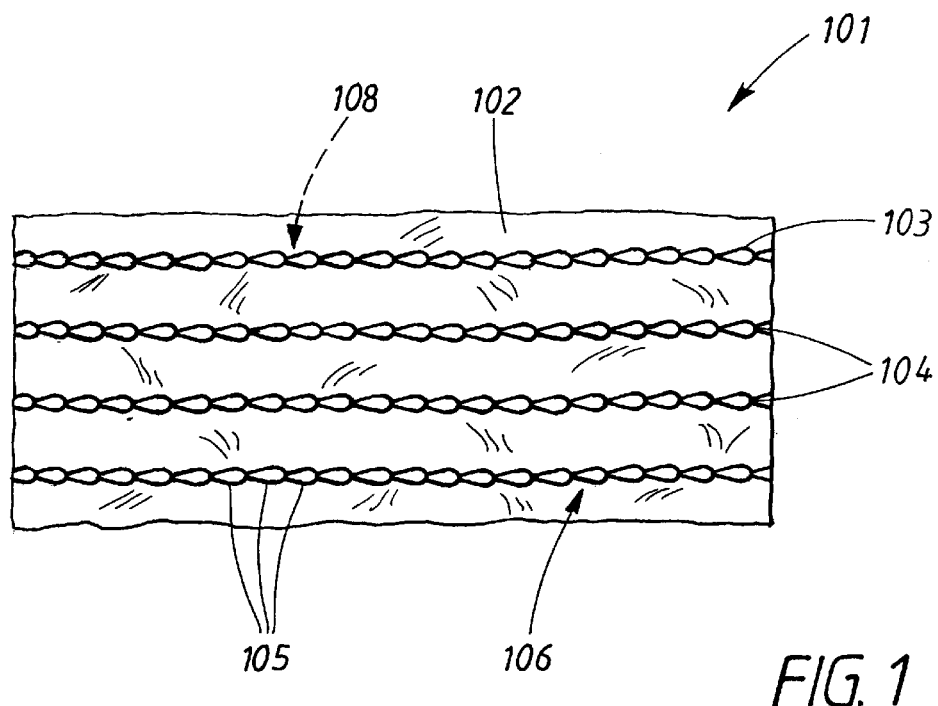
FIG. 1 shows a fastening member provided with loops.
Figure 2:
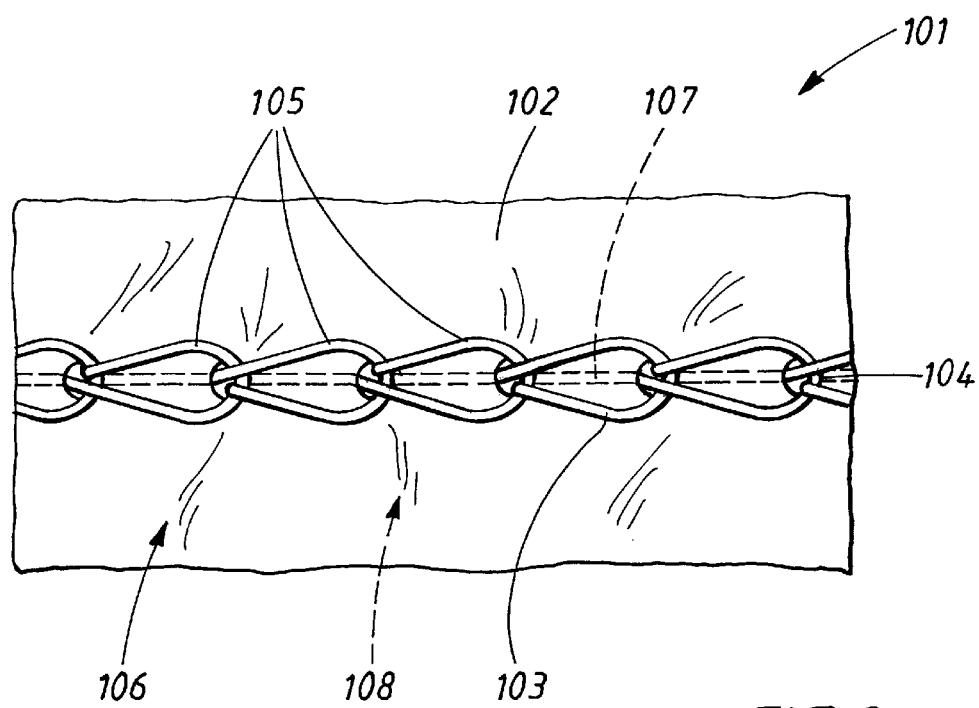
FIG. 2 shows in detail a row of loops on the fastening member in FIG. 1.

FIGS. 1 and 2 show a fastening member 101 provided with loops 105. The fastening member 1001 may include a carrier material 102 which has a thread 103 forming a chain-like row 104 of fastening loops 105 on a first surface 106 of the carrier material 102, where the fastening loops 105 are linked together by a row of thread elements 107 forming straight stitches on the opposite, second surface 108 of the carrier material 102. Alternatively, the fastening loops 105 may be sewn directly into the article to be fastened, e.g., a belt.

The carrier material 102 comprises a layer material, such as plastic film, nonwoven, or a laminate of two or more layers of plastic film, nonwoven, tissue or the like. The carrier material preferably comprises a layer of a nonwoven with a stiffness of 0.10–0.70 N, and preferably with a stiffness of 0.35 N, measured according to the CIRCULAR BEND PROCEDURE which is described in U.S. Pat. No.

5,009,653. A particularly preferred material, with a stiffness suitable for the purpose, has been found to be a spunbond material with a grammage of at least about 60 g/m$^2$ and preferably about 80 g/m$^2$.

The thread that forms the fastening loops 105 can be of any suitable material and can comprise synthetic and/or natural fibers. Thus, it is possible to use fibers of polyethylene, polypropylene, polyester, polyamide or two-component fibers such as cotton fibers, jute, flax, etc. The thread is advantageously bulky and comprises in cross section a plurality of thin and substantially parallel fibers. It is also advantageous if the fibers have a certain curl, since this increases the bulkiness and increases the thread's ability to cooperate with a hook member for fastening an absorbent article.

The fastening member 101 comprises a plurality of rows 104 of fastening loops 105, as is shown in FIG. 1.

Figure 3:
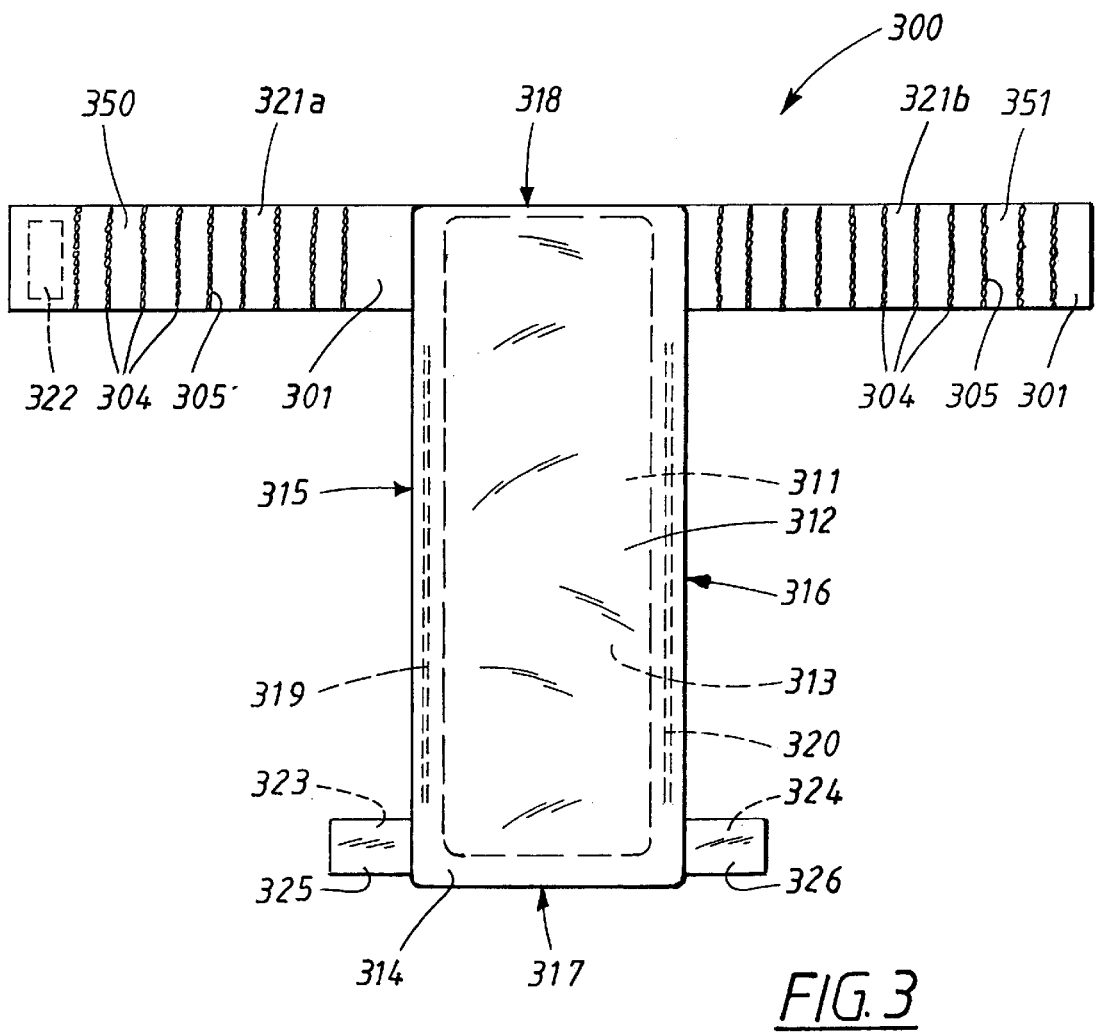
FIG. 3 shows a plan view of a belted diaper according to the invention, seen from the side which is directed away from the user during use.
Figure 4:
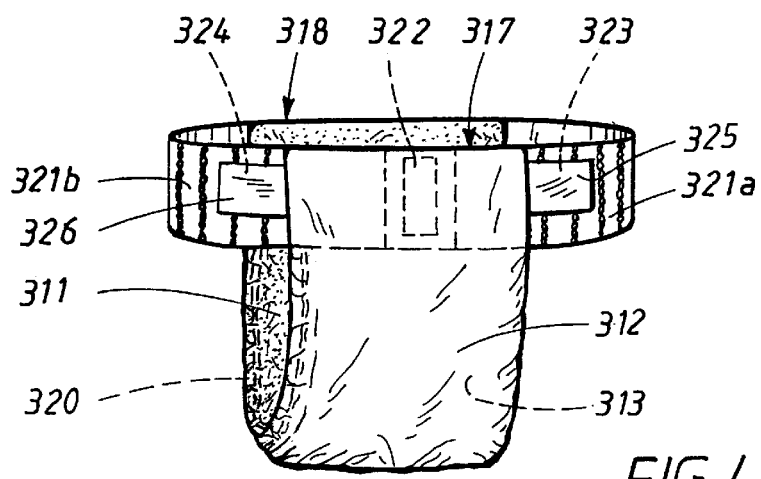
FIG. 4 shows the diaper from FIG. 3 as it appears when it has been fastened up.

FIGS. 3 and 4 show a diaper 300 with a substantially rectangular plane shape. The diaper 300 is seen from the side which is intended to be directed away from the user during use. The diaper comprises, in a conventional manner, a liquid-permeable cover sheet 311, a liquid-tight cover sheet 312, and an absorption body 313 enclosed between the cover sheets 311, 312.

The liquid-permeable cover sheet 311 has the same shape as the absorption body 313. The liquid-tight cover sheet 312 is also shaped like the absorption body. However, the cover sheets 311, 312 have a slightly greater planar extent than the absorption body 313 and form a connecting edge 314 projecting around the periphery of the absorption body 313. The cover sheets 311, 312 are connected to each other around the absorption body, for example by adhesive bonding, stitching, or welding with heat or ultrasound. One or both cover sheets 311, 312 can also be connected to the absorption body 313, for example by adhesive bonding, pinning, stitching, or welding with heat or ultrasound.

The liquid-permeable cover sheet 311 is of a conventional type and can thus comprise any liquid-permeable material suitable for the purpose. Examples of such materials are different types of thin nonwoven material, perforated plastic films, net material, liquid-permeable foam material, or the like. The liquid-permeable cover sheet 311 can be made up of two or more different materials in order to permit different functions of the cover sheet. For example, it is common to arrange a liquid-transporting layer inside a liquid admission layer. It is also known to arrange different types of material on different parts of that surface of the diaper which is directed towards the user during use. Thus, a material with a good admission capacity can advantageously be arranged on that portion of the diaper which is expected to be first wetted by most of the body fluid, while portions of the cover sheet which are located at a distance from the first wetted area can be designed with a barrier function in order to prevent absorbed liquid from leaking out of the diaper.

Nor is it necessary to the invention for the liquid-permeable cover sheet 311 to comprise a separate material layer, and instead the cover sheet 311 can be a surface of the absorption body 313 of the diaper 300.

The liquid-tight cover sheet 312 can also be made of any suitable material available. Particularly advantageous materials are thin plastic films, liquid-tight nonwoven material, or material which has been coated with liquid-tight material such as wax, resin, glue or the like. It is also possible to use liquid-tight material laminates. For example, it can be desirable to provide the rear side of the diaper with an outer layer of textile character, as in a nonwoven layer. Such a non-woven material provides a soft, skin-friendly textile surface and gives advantages such as a high degree of user comfort, high friction and, consequently, a better hold on the articles of clothing worn outside the diaper. In addition, a textile surface is often found to have an esthetically attractive appearance. It is also advantageous if the liquid-tight cover sheet 312 is able to breathe, i.e., allow gas and water vapor to pass through the layer.

The absorption body 313 can also be designed in a conventional manner and using conventional material. Suitable absorbent materials for use in the absorption body 313 are, for example, cellulose fluff pulp, absorbent bonded fiber layers, tissue layers, absorbent foam, peat or the like. The absorption body 313 can also advantageously contain super-absorbent polymers, i.e. polymers having the ability to absorb several times their own weight of liquid and form a liquid gel. Superabsorbents are generally used in the form of particles, flakes, fibers, granules, or the like. The superabsorbent material can be present on its own, or together with another absorbent material and arranged as layers, or in the form of a mixture with other materials such as cellulose fibers or synthetic fibers.

As has already been mentioned, the diaper 300 in FIGS. 3 and 4 is substantially rectangular in shape and has two straight side edges 315, 316 and two likewise straight end edges 317, 318.

Elastic members 319, 320 are arranged along the side edges 315, 316 and form leg elastics when the diaper 300 is in use. Suitable elastic members are various types of elastic threads, bands, elastic nonwovens, elastic foam material, or the like.

The diaper 300 is also provided with a two-part waist belt 321a,b, which is arranged with a belt half 321a,b projecting at right angles from each side edge 315, 316 near the rear end edge 318 of the diaper. The belt halves 321a,b preferably comprise strips of nonwoven material having a large number of parallel chain-like rows 304 of fastening loops 305 forming a fastening member 301, provided with loops, of the type shown in FIGS. 1 and 2. However, as has been described earlier, the fastening member 301 can alternatively consist of a plastic film or laminate material. The fastening member 301 can also be laminated to a further material layer whose main purpose is to give the waist belt a desired property such as improved softness and comfort, greater tensile strength and more esthetically attractive appearance, a certain elasticity, a certain absorbency, etc. The chain-like rows 304 of fastening loops are arranged on the surface of the waist belt 321a,b that is directed away from the user when the diaper 300 is being used, i.e., the surface which in FIG. 3 is directed towards the viewer. The rows 304 of fastening loops 305 are also arranged transverse to the waist belt 321a,b, in the longitudinal direction of the diaper 300.

Alternatively, the fastening loops 305 may be sewn directly into the belt material, without the use of a carrier material.

To ensure that the diaper 300 can be fastened together into a garment similar to underpants when in use, the diaper is additionally provided with fastening members 322, 323, 324 which have hook members. One fastening member 322 provided with hooks is in this case arranged on the free end 350 of one belt half 321a, on the surface that is directed away from the fastening member 301 provided with loops. Fastening flaps 325, 326 are also arranged projecting from the side edges 315, 316 at the front end edge 317. The fastening flaps 325, 326 have fastening members 323, 324 provided with hooks on the surface that is directed away from the viewer of FIG. 3, i.e., the surface that is directed towards the user when the diaper is in use. Alternatively, the belt 321a,b may have hook members, and the fastening members 322, 323, 324 may have loop members.

In this context, hook members are intended to signify all existing types of hooks, catches and projections which can hook into the loops 305 on the fastening member 301 provided with loops.

When it is being used, the diaper 300 is secured around the lower part of the user's trunk and then assumes the shape shown in FIG. 4. This is done by means of the free end portions 350, 351 of both halves 321a,b of the waist belt being brought together around the user's waist and by means of the fastening member 322, provided with hooks, on one belt half 312a of the waist belt being secured in the fastening loops on the other belt half 321b. The front end edge 317 of the diaper is then guided forward between the user's legs and secured by means of the fastening members 323, 324, provided with hooks, on the fastening flaps 325, 326 being applied against the fastening member 301, provided with loops, on the waist belt 321a,b.

Figure 5:
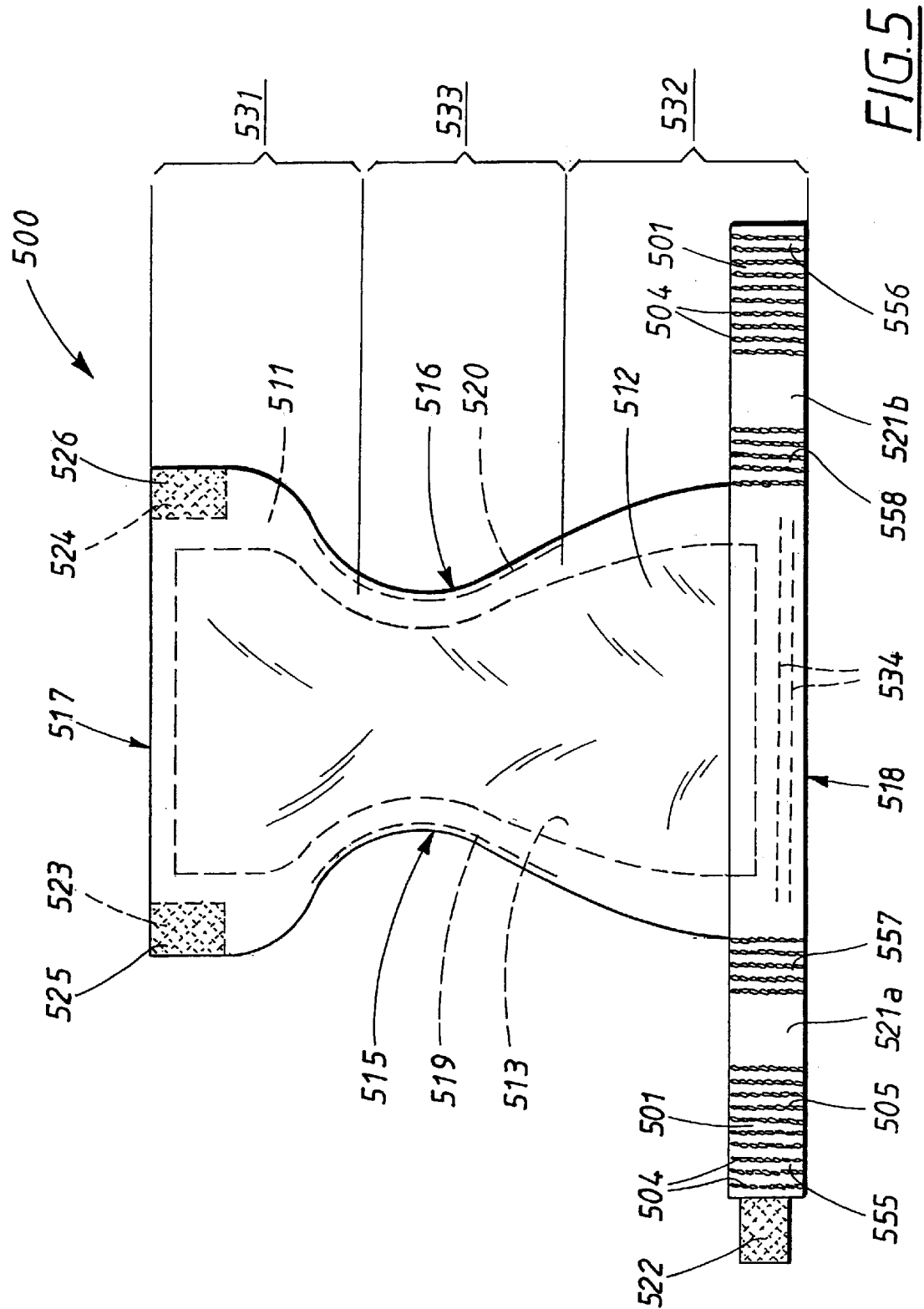
FIG. 5 shows a diaper according to a second embodiment of the invention.

The diaper 500 shown in FIG. 5 is also viewed from the side directed away from the user during use and comprises, in a corresponding manner, a liquid-permeable cover sheet 511, a liquid-tight cover sheet 512, and an absorption body 513 enclosed between the cover sheets 511, 512. The diaper is substantially hourglass-shaped, with a front portion and a rear portion 531, 532 and with an intermediate narrower crotch portion 533. The diaper also has two curved side edges 515, 516 that are designed to form rounded openings around a user's legs when the diaper is fitted on the user, and a front and a rear end edge 517, 518, which, during use, together form the waist edge of the diaper. The diaper 500 additionally has elastic members 519, 520 arranged along the curved side edges and intended to gather the diaper together around the user's legs so that a tight fit is obtained around the legs. Elastic members 534 are correspondingly arranged along the rear end edge 518 in order to obtain a good fit around the user's waist.

The diaper 500 shown in FIG. 5 also has a waist belt 521 comprising a fastening member 501 provided with loops. However, in contrast to the diaper shown in FIGS. 3 and 4, the diaper 500 in FIG. 5 has a continuous waist belt 521 that extends along the entire rear edge 518 of the diaper 500 and extends in the transverse direction past the side edges 515, 516 of the diaper via portions 521a, 521b that are sufficiently long for the waist belt 512 to be able to reach around a user's waist. The elastic members 534 on the rear waist edge 518 are, in this case, arranged in the waist belt 521. As can be seen from the figure, the fastening member 501 provided with loops 505 is arranged in the form of a multiplicity of rows 504 of loops that extend across the waist belt via the free end portions 550, 551 of its two projecting portions 521a, 521b. The rows 504 of loops 505 are arranged in the areas 555, 556 of the waist belt 521 that are expected to be used for fastening the diaper 500 together. A further area 557, 558 of rows of loops is also arranged on both sides of the elastic members 534 at the rear waist edge 518 in order to prevent the waist belt 521 from creasing up or being folded within the elastic area.

It should be pointed out that the invention is, of course, not limited to the examples shown in FIGS. 3–5 in terms of how the rows 304, 504 of loops can be arranged on a waist belt. It is thus possible to conceive of rows of loops being grouped in another way than that shown in FIG. 5. For example, the whole waist belt, or at least those portions which are intended to be used for fastening, can be provided with groups of 2–20 rows of loops alternating with areas which are free from rows of loops. The free areas in this case have a width that exceeds the spacing between the rows of loops within the groups and is expediently between 5 and 100 mm. The rows 304, 504 of loops perform the dual function of serving as fastening members and as stiffening/stabilizing members for the waist belt 321a,b, 521 in order to prevent rolling and folding.

So that the diaper 500 can be fastened together into a garment similar to underpants when in use, a fastening member in the form of a fastening flap 522 and having hook members is arranged at the free end of one projecting portion 521a of the waist belt 521. The fastening flap 522 is arranged with the hook members on that surface which is directed away from the fastening members 501, provided with loops, of the waist belt. Fastening members in the form of fastening surfaces 525, 526 are also arranged projecting inside the side edges 515, 516 near the front end edge 517. The fastening surfaces 525, 526 have fastening members 523, 524, provided with hooks, on the surface that is directed away from the person viewing FIG. 5, i.e. the surface which is directed towards the user when the diaper is in use. Alternatively, the belt 521 may have hook members, and the fastening members surfaces 525, 526 and the fastening flap 522 may have loop members.

When in use, the diaper 500 is secured around the lower part of the user's trunk in the same way as the diaper in FIGS. 3 and 4 and then assumes the appearance of underpants. This is done by means of the two projecting portions 521a, 521b of the waist belt being brought together around the user's waist and by means of the fastening flap 522, provided with hooks, on one projecting portion 521a of the waist belt 521 being secured in the fastening loops on the other projecting portion of the waist belt 521. The front end edge 517 of the diaper is then guided forwards between the user's legs and secured by means of the hook members 523, 524 on the fastening surfaces 525, 526 against the fastening member 501, provided with loops, on the waist belt 521.

The arrangement shown in FIG. 5 with fastening surfaces 525, 526, provided with hooks, placed at the corners between the rear end edge 518 and the side edges 515, 516 on the liquid-permeable cover sheet 511 of the diaper 500 can of course be replaced by fastening flaps as are shown in FIGS. 3 and 4. Likewise, the fastening member 522, provided with hooks, on the waist belt can be designed in the same way as in the case of the diaper in FIGS. 3 and 4. Conversely, of course, the diaper 300 in FIGS. 3 and 4 can have fastening surfaces 322, 325, 326, provided with hooks, arranged in the manner shown in FIG. 5. According to yet another alternative, the fastening members 325, 326; 525, 526 at the front end edge 317; 517 of the diapers shown in the figures can be designed as a single continuous fastening area, provided with hooks, or as a plurality of fastening areas arranged along the front end edge 317; 517.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent article with a longitudinal direction and a transverse direction, comprising:

a liquid-permeable cover sheet, a liquid-tight cover sheet, an absorption body enclosed between the cover sheets, two side edges extending in the longitudinal direction, two end edges extending in the transverse direction, a waist belt formed by at least one material layer and arranged substantially parallel to one of the end edges of the article, the waist belt has two free ends each comprising a first fastening member having a surface provided with fastening loops that are designed to cooperate with a fastening member comprising hook members, the fastening loops are arranged in a number of chain-like rows, each chain-like row formed by a continuous thread that penetrates through at least the material layer included in the waist belt, the chain-like rows of loops are arranged principally in the longitudinal direction of the article, at right angles to a direction of extent of the waist belt, and a second fastening member arranged on the end edge of the article opposite the waist belt, the second fastening member has hook members that are arranged to cooperate with the first fastening members in order to fasten the article into a shape similar to underpants, wherein the waist belt at least partially comprises a nonwoven material with a stiffness of 0.10–0.70 N measured according to a modified version of ASTM D 4032-82, CIRCULAR BEND PROCEDURE.

2. The absorbent article as claimed in claim 1, wherein the waist belt includes a third fastening member arranged in the form of a fastening surface or a fastening flap at a free end of the waist belt and which can cooperate with the first fastening members provided with loops on the waist belt in order to fasten the waist belt around a user's waist.

3. The absorbent article as claimed in claim 1, wherein the waist belt comprises a nonwoven material with a basis weight of 40 g/m$^2$ to 80 g/m$^2$.

4. The absorbent article as claimed in claim 1, wherein the fastening loops have a length of 2–10 mm.

5. The absorbent article as claimed in claim 1, wherein the chain-like rows of loops are uniformly distributed across a whole surface of the waist belt, and wherein the spacing between the rows of loops is 1–10 mm.

6. The absorbent article as claimed in claim 1, wherein each of the first fastening members has at least one group of chain-like rows of loops that comprise at least two chain-like rows of loops.

7. The absorbent article as claimed in claim 6, wherein each belt end has at least two groups of chain-like rows of loops, and wherein the chain-like rows of loops within the groups are situated at a spacing of 1–10 mm from each other and the spacing between the groups is greater than the spacing between the chain-like rows of loops within the groups and is 5–100 mm.

8. The absorbent article as claimed in claim 1, wherein the waist belt comprises a continuous integral band of material.

9. The absorbent article as claimed in claim 1, wherein the waist belt consists of two belt halves that project substantially at right angles from each side edge at one end edge of the article.

10. The absorbent article as claimed in claim 1, wherein the continuous thread that forms the chain-like rows of loops has a coarseness of 20–90 deniers.

11. The absorbent article as claimed in claim 1, wherein the waist belt at least partially comprises a non-woven material with a stiffness of 0.35 N measured according to a modified version of ASTM D 4032-82, CIRCULAR BEND PROCEDURE.

12. The absorbent article as claimed in claim 1, wherein the second fastening member is arranged to cooperate with the first fastening members on an outwardly facing surface of the waist belt.

* * * * *